US008633136B2

(12) United States Patent
Iskandar et al.

(10) Patent No.: US 8,633,136 B2
(45) Date of Patent: Jan. 21, 2014

(54) AGRICULTURAL ADJUVANT COMPOSITIONS, PESTICIDE COMPOSITIONS, AND METHODS FOR USING SUCH COMPOSITIONS

(75) Inventors: Sahar Iskandar, Dayton, NJ (US); Rajesh Pazhianur, Yardley, PA (US)

(73) Assignee: Rhodia Operations, Aubervilliers (FR)

( * ) Notice: Subject to any disclaimer, the term of this patent is extended or adjusted under 35 U.S.C. 154(b) by 0 days.

(21) Appl. No.: 13/411,206

(22) Filed: Mar. 2, 2012

(65) Prior Publication Data

US 2012/0165195 A1 Jun. 28, 2012

Related U.S. Application Data

(62) Division of application No. 12/444,685, filed as application No. PCT/US2007/022094 on Oct. 16, 2007, now abandoned.

(60) Provisional application No. 60/851,947, filed on Oct. 16, 2006.

(51) Int. Cl.
*A01N 57/18* (2006.01)
*A01N 25/00* (2006.01)

(52) U.S. Cl.
USPC .......................................... 504/206; 504/358

(58) Field of Classification Search
USPC ................................................ 504/206, 358
See application file for complete search history.

(56) References Cited

U.S. PATENT DOCUMENTS

| | | |
|---|---|---|
| 3,225,074 A | 12/1965 | Cowen et al. |
| 3,527,593 A | 9/1970 | Bland et al. |
| 3,723,357 A | 3/1973 | Hansen |
| 3,882,051 A | 5/1975 | Hansen |
| 4,011,388 A | 3/1977 | Murphy et al. |
| 4,107,328 A | 8/1978 | Michaels |
| 4,117,107 A | 9/1978 | Shapiro |
| 4,122,159 A | 10/1978 | Madrange et al. |
| 4,137,191 A | 1/1979 | Lohr |
| 4,243,549 A | 1/1981 | Messenger et al. |
| 4,452,732 A | 6/1984 | Bolich, Jr. |
| 4,477,365 A | 10/1984 | Verboom et al. |
| 4,585,846 A | 4/1986 | Schulz et al. |
| 4,607,076 A | 8/1986 | Schulz et al. |
| 4,650,848 A | 3/1987 | Schulz et al. |
| 4,703,797 A | 11/1987 | Djabbarah |
| 4,708,998 A | 11/1987 | Schulz et al. |
| 4,742,135 A | 5/1988 | Schulz et al. |
| 4,788,247 A | 11/1988 | Schulz et al. |
| 4,822,847 A | 4/1989 | Schulz et al. |
| 4,831,092 A | 5/1989 | Bock et al. |
| 4,835,234 A | 5/1989 | Valint et al. |
| 4,882,405 A | 11/1989 | Schulz et al. |
| 4,996,045 A | 2/1991 | Leighton et al. |
| 5,153,289 A | 10/1992 | Schulz et al. |
| 5,164,120 A | 11/1992 | Borland et al. |
| 5,180,414 A | 1/1993 | Darchy et al. |
| 5,258,358 A | 11/1993 | Kocur et al. |
| 5,292,942 A | 3/1994 | Aigner et al. |
| 5,338,793 A | 8/1994 | Loftin |
| 5,341,932 A | 8/1994 | Chen et al. |
| 5,354,906 A | 10/1994 | Weitemeyer et al. |
| 5,385,206 A | 1/1995 | Thomas |
| 5,439,317 A | 8/1995 | Bishop et al. |
| 5,464,806 A | 11/1995 | Kassebaum et al. |
| 5,551,516 A | 9/1996 | Norman et al. |
| 5,580,856 A | 12/1996 | Prestrelski et al. |
| 5,612,285 A | 3/1997 | Arnold |
| 5,686,400 A | 11/1997 | Urfer et al. |
| 5,700,760 A | 12/1997 | Magin et al. |
| 5,703,016 A | 12/1997 | Magin et al. |
| 5,747,416 A | 5/1998 | McArdle et al. |
| 5,863,863 A | 1/1999 | Hasebe et al. |
| 5,874,394 A | 2/1999 | Thomas et al. |
| 5,877,143 A | 3/1999 | Abbas et al. |
| 5,888,934 A | 3/1999 | Townson et al. |
| 5,897,699 A | 4/1999 | Chatterji et al. |
| 5,912,209 A | 6/1999 | Kassebaum et al. |
| 5,985,798 A | 11/1999 | Crudden |
| 5,998,332 A * | 12/1999 | Sato et al. ..................... 504/127 |

(Continued)

FOREIGN PATENT DOCUMENTS

| | | |
|---|---|---|
| CA | 2554335 | 8/2005 |
| EP | 0373851 | 6/1990 |

(Continued)

OTHER PUBLICATIONS

Ullmann's Encyclopedia of Industrial Chemistry, 5th Ed., vol. A 10, Edited by Gerhartz et al., pp. 176-177, Wiley-VCH Verlag GmbH & Co. KGaA, Weinheim, Germany, May 5, 1994.
"Application Guide for Household & Industrial Markets"; McIntyre Group Ltd., Copyright 2002, (Jan. 2003), obtained online @ http://www.dewolfchem.com/pdf/Mcintyre_HI&I_Application_Guide.pdf, (downloaded Mar. 6, 2012).
Surfactants by Albright & Wilson (Australia Limited CAN 004 234 137)—5 pp.
Empigen BB-AU alkyl betaine by Albright & Wilson Australia Limited (Incorporated in Victoria) Product Handling & Safety Bulletin—4 pp , Feb. 1994.

(Continued)

*Primary Examiner* — Sue Liu
*Assistant Examiner* — Andriae M Holt
(74) *Attorney, Agent, or Firm* — Novak Druce Connolly Bove + Quigg, LLP

(57) ABSTRACT

An adjuvant composition for use with a pesticide contains at least one surfactant compound selected from each of at least two of the following groups:(i) phosphate ester surfactants, (ii) alkylpolyglucoside surfactants, (iii) the group consisting of imidazoline-based amphoteric surfactants, sultaine surfactants, and aminopropionate surfactants, and (iv) the group consisting of sulfonate surfactants, sulfosuccinate surfactants, alkyl ether carboxylate surfactants, alkoxylated fatty acid surfactants, and alkoxylated alcohol surfactants. A pesticide composition contains the adjuvant composition and a pesticide is useful for treating plants.

9 Claims, No Drawings

(56) References Cited

U.S. PATENT DOCUMENTS

| | | |
|---|---|---|
| 6,030,928 A | 2/2000 | Stahl et al. |
| 6,036,638 A | 3/2000 | Nwawka |
| 6,127,318 A | 10/2000 | Sato et al. |
| 6,165,939 A | 12/2000 | Agbaje et al. |
| 6,210,476 B1 | 4/2001 | Chatterji et al. |
| 6,284,854 B1 | 9/2001 | Bowers et al. |
| 6,288,010 B1 | 9/2001 | Rose et al. |
| 6,299,798 B1 * | 10/2001 | Guerin et al. ............ 252/363.5 |
| 6,302,209 B1 | 10/2001 | Thompson et al. |
| 6,329,322 B1 | 12/2001 | Reierson |
| 6,346,588 B1 | 2/2002 | Fench et al. |
| 6,369,122 B1 | 4/2002 | Subramanyam |
| 6,376,566 B1 | 4/2002 | Bergeron et al. |
| 6,407,042 B1 | 6/2002 | Ward et al. |
| 6,417,268 B1 | 7/2002 | Zhang et al. |
| 6,432,878 B1 | 8/2002 | Brigance |
| 6,432,884 B1 | 8/2002 | Lachut |
| 6,451,731 B1 | 9/2002 | Agbaje et al. |
| 6,500,784 B1 | 12/2002 | Mille et al. |
| 6,566,408 B1 | 5/2003 | Cotrell et al. |
| 6,642,178 B2 | 11/2003 | Woznica et al. |
| 6,645,912 B1 | 11/2003 | Mille et al. |
| 6,645,914 B1 | 11/2003 | Woznica et al. |
| 6,653,257 B2 | 11/2003 | Mille et al. |
| 6,770,268 B1 | 8/2004 | Hall et al. |
| 6,770,594 B2 | 8/2004 | Bickers et al. |
| 6,831,108 B2 | 12/2004 | Dahanayake et al. |
| 6,881,707 B2 | 4/2005 | Howat et al. |
| 6,992,046 B2 | 1/2006 | Bramati et al. |
| 7,135,437 B2 | 11/2006 | Pallas et al. |
| 7,316,990 B2 | 1/2008 | Tank et al. |
| 8,236,730 B2 | 8/2012 | Bramati et al. |
| 8,263,529 B2 | 9/2012 | Suzuki et al. |
| 8,383,137 B2 | 2/2013 | Modaressi et al. |
| 2002/0187917 A1 | 12/2002 | Lazarowitz |
| 2003/0118540 A1 | 6/2003 | Charlton et al. |
| 2004/0097372 A1 | 5/2004 | Abraham et al. |
| 2004/0110644 A1 | 6/2004 | Halliday et al. |
| 2004/0121917 A1 | 6/2004 | Pakulski |
| 2005/0003965 A1 | 1/2005 | Xiao et al. |
| 2005/0010009 A1 | 1/2005 | Schulz et al. |
| 2005/0020454 A1 | 1/2005 | Francini et al. |
| 2005/0130842 A1 | 6/2005 | Fleute-Schlachter |
| 2005/0170965 A1 | 8/2005 | Bramati et al. |
| 2006/0019830 A1 | 1/2006 | Xu et al. |
| 2006/0060354 A1 | 3/2006 | Lewis et al. |
| 2007/0155628 A1 | 7/2007 | Pazhianur et al. |
| 2007/0282075 A1 | 12/2007 | Koch et al. |
| 2008/0103047 A1 | 5/2008 | Gioia et al. |
| 2008/0312083 A1 | 12/2008 | Gioia et al. |
| 2009/0018018 A1 | 1/2009 | Gioia et al. |
| 2010/0069269 A1 | 3/2010 | Prat et al. |
| 2010/0093874 A1 | 4/2010 | Monin et al. |
| 2010/0140531 A1 | 6/2010 | Prat et al. |
| 2011/0009269 A1 | 1/2011 | Gioia et al. |
| 2011/0015071 A1 | 1/2011 | Kisenwether et al. |
| 2012/0040833 A1 | 2/2012 | Kisenwether et al. |

FOREIGN PATENT DOCUMENTS

| | | |
|---|---|---|
| EP | 0274369 | 9/1990 |
| EP | 0483095 | 10/1991 |
| EP | 0370338 | 5/1992 |
| EP | 0508022 | 10/1992 |
| EP | 0573118 | 12/1993 |
| EP | 0449159 | 7/1995 |
| EP | 0810239 | 9/2000 |
| JP | 11-349826 | 6/1998 |
| JP | 10183176 | 7/1998 |
| WO | 9212637 | 8/1992 |
| WO | 92/14907 | 9/1992 |
| WO | 9701281 | 1/1997 |
| WO | 9706230 | 2/1997 |
| WO | 97/36489 | 10/1997 |
| WO | 98/14060 | 4/1998 |
| WO | 99/03895 | 1/1999 |
| WO | 99/15610 | 4/1999 |
| WO | 9945780 | 9/1999 |
| WO | 99/62338 | 12/1999 |
| WO | 0038523 | 7/2000 |
| WO | 0067571 | 11/2000 |
| WO | 0067573 | 11/2000 |
| WO | 0108482 | 2/2001 |
| WO | 0117358 | 3/2001 |
| WO | 0126463 | 4/2001 |
| WO | 0126469 | 4/2001 |
| WO | 0189302 | 11/2001 |
| WO | 02/26036 | 4/2002 |
| WO | 03/049813 | 6/2003 |
| WO | 2004/107861 | 12/2004 |
| WO | 2004107862 | 12/2004 |
| WO | 2007003112 | 1/2007 |

OTHER PUBLICATIONS

Basheva et al.; Role of Betaine as Foam Booster in the Presence of Silicone Oil Drops; Langmuir 2000, 16, 1000-1013; 2000 American Chemical Society Published on Web Dec. 8, 1999.

* cited by examiner

AGRICULTURAL ADJUVANT COMPOSITIONS, PESTICIDE COMPOSITIONS, AND METHODS FOR USING SUCH COMPOSITIONS

CROSS-REFERENCE TO RELATED APPLICATIONS

This application is a divisional application of U.S. application Ser. No. 12/444,685 filed on May 14, 2009 which is a §371 National Stage Application of International Application No. PCT/US2007/022094, filed on Oct. 16, 2007, incorporated herein by reference, which claims the benefit of U.S. Provisional Appl No. 60/851,947, filed Oct. 16, 2006.

FIELD OF THE INVENTION

This invention relates to agricultural adjuvant compositions, pesticide compositions, and methods for using such compositions.

BACKGROUND OF THE INVENTION

Many agricultural pesticides, including insecticides, fungicides, herbicides, miticides, and plant growth regulators, are applied in the form of a liquid composition. In addition to the pesticide and a solvent, such liquid compositions typically include one or more adjuvant compounds intended to improve one or more properties of the liquid composition, such as for example, storage stability, ease of handling, and pesticide efficacy against target organisms.

There is a continuing interest in pesticide compositions that exhibit improved properties.

SUMMARY OF THE INVENTION

In a first aspect, the present invention is directed to an adjuvant composition comprising at least one surfactant compound selected from each of at least two of the following groups:
(i) phosphate ester surfactants,
(ii) alkylpolyglucoside surfactants,
(iii) the group consisting of imidazoline-based amphoteric surfactants, sultaine surfactants, and aminopropionate surfactants, and
(iv) the group consisting of sulfonate surfactants, sulfosuccinate surfactants, alkyl ether carboxylate surfactants, alkoxylated fatty acid surfactants, and alkoxylated alcohol surfactants.

In a second aspect, the present invention is directed to a pesticide composition, comprising
(a) at least one surfactant compound selected from each of at least two of the following groups:
(i) phosphate ester surfactants,
(ii) alkylpolyglucoside surfactants,
(iii) the group consisting of imidazoline-based amphoteric surfactants, sultaine surfactants, and aminopropionate surfactants, and
(iv) the group consisting of sulfonate surfactants, sulfosuccinate surfactants, alkyl ether carboxylate surfactants, alkoxylated fatty acid surfactants, and alkoxylated alcohol surfactants, and
(b) an effective amount of a pesticide.

In a third aspect, the present invention is directed to a method for treating a target plant, comprising applying the above described pesticide composition to such plant.

DETAILED DESCRIPTION OF INVENTION AND PREFERRED EMBODIMENTS

As used herein, the term "alkyl" means a saturated straight chain, branched chain, or cyclic hydrocarbon radical, such as for example, methyl, ethyl, n-propyl, iso-propyl, n-butyl, sec-butyl, t-butyl, pentyl, n-hexyl, and cyclohexyl.

As used herein, the term "alkylene" means a divalent saturated straight or branched chain hydrocarbon radical, such as for example, methylene, dimethylene, trimethylene.

As used herein, the term "alkoxy" means an oxy radical that is substituted with an alkyl group, such as for example, methoxy, ethoxy, propoxy, isopropoxy, and butoxy. As used herein in reference to an organic compound, the term "alkoxylated" means that the compound comprises one or more alkoxy or, more typically, poly(alkyleneoxy) moieties, such as, for example a poly(ethyleneoxy), poly(propyleneoxy), or poly(ethlyeneoxypropyleneoxy) moiety and the term "ethoxylated" means that the compound comprises at least one ethoxy or poly(ethyleneoxy) moiety. As used herein in reference to a poly(alkyleneoxy) moiety, the notation "(n)", wherein n is an integer, indicates the number of alkyleneoxy monomeric units in the poly(alkyleneoxy) moiety. For example such as " ethoxylated (15) tridecyl alcohol" means a tridecyl alcohol ethoxylated with 15 moles of ethyleneoxy units per mole of tridecyl alcohol.

As used herein, the term "alkenyl" means an unsaturated straight chain, branched chain, or cyclic hydrocarbon radical that contains one or more carbon-carbon double bonds, such as, for example, ethenyl, 1-propenyl, and 2-propenyl.

As used herein, the term "aryl" means a monovalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenoxy, phenyl, methylphenyl, dimethylphenyl, trimethylphenyl, chlorophenyl, trichloromethylphenyl, aminophenyl, and tristyrylphenyl.

As used herein, the term "arylene" means a divalent unsaturated hydrocarbon radical containing one or more six-membered carbon rings in which the unsaturation may be represented by three conjugated double bonds, which may be substituted one or more of carbons of the ring with hydroxy, alkyl, alkenyl, halo, haloalkyl, or amino, such as, for example, phenylene, methylphenylene, trimethylphenylene, aminophenylene and tristyrylphenylene.

As used herein, the term "aralkyl" means an alkyl group substituted with one or more aryl groups, such as, for example, phenylmethyl, phenylethyl, and triphenylmethyl.

As used herein, the term "aralkenyl" means an alkenyl group substituted with an aryl group, such as, for example, phenylethenyl, and phenylpropenyl.

As used herein, the term "aryloxy" means an oxygen radical substituted with an aryl group, such as, for example, phenoxy, methylphenoxy, and trimethylphenoxy.

As used herein, the terminology "($C_n$-$C_m$)" in reference to an organic group, wherein n and m are each integers, indicates that the group may contain from n carbon atoms to m carbon atoms per group.

As used herein, the term "agronomically acceptable salts" refers to salts prepared from agronomically acceptable non-toxic bases or acids including inorganic or organic bases and inorganic or organic acids. Typical agronomically acceptable salts the compound referred to herein comprise an anion derived from the compound, for example, by deprotonation of a hydroxy or hydroxyalkyl substituent, and one or more positively charged counterions. Suitable positively charged counterions include inorganic cations and organic cations, such as for example, sodium cations, potassium cations, calcium cations, magnesium cations, isopropylamine cations, ammonium cations, and tetraalkylammonium cations.

As used herein, the term "surfactant" means a compound that, when dissolved in a liquid, reduces surface tension of the liquid, which reduces interfacial tension between two liquids or which reduces surface tension between a liquid and a solid. More typically the term "surfactant" is used herein to refer to a compound that, when dissolved in water, reduces the surface tension of the water.

Phosphate ester surfactants are generally known. In one embodiment, the phosphate ester surfactant comprises one or more compounds according to structure (I):

$$R^1-O-(C_mH_{2m}O)_n-\overset{\overset{O}{\|}}{\underset{OH}{P}}-(OC_{m'}H_{2m'})_{n'}-O-R^2 \quad (I)$$

wherein:

$R^1$ and $R^2$ are each independently H, alkyl, alkenyl, aryl, or alkaryl, provided that at least one of $R^1$ and $R^2$ is alkyl, alkenyl, aryl, or alkaryl m and m' are each 2, 3, or 4, provided, if n is greater than 1, that m may differ independently for each $(C_mH_{2m}O)$ repeat unit, and if n' is greater than 1, that m' may differ independently for each $(C_mH_{2m}O)$ repeat unit, and n and n' are each independently 0 or an integer of from 1 to about 20.

or an agronomically acceptable salt thereof.

In one embodiment, $R^1$ and $R^2$ are each independently H, $(C_4-C_{22})$alkyl, more typically, $(C_4-C_{18})$alkyl, or $(C_4-C_{22})$alkenyl, more typically, $(C_4-C_{18})$alkenyl, and n and n' are each independently 0 or an integer of from 1 to about 6.

Suitable phosphate ester surfactants include, for example, butyl phosphate, ethoxylate butyl phosphate, dibutyl phosphate, ethoxylated dibutyl phosphate, hexyl phosphate, dihexyl phosphate, 2-ethylhexylphosphate, di-2-ethylhexyl phosphate, octyl phosphate, ethoxylated octyl phosphate dioctyl phosphate, ethoxylated dioctyl phosphate, decyl phosphate, didecyl phosphate, stearyl phosphate, ethoxylated stearyl phosphate, distearyl phosphate, ethoxylated distearyl phosphate and mixtures thereof Alkylpolyglucoside surfactants are generally known. In one embodiment, the alkylpolyglucoside surfactant comprises one or more compounds according to structure (II):

(II)

wherein $R^3$ is alkyl, hydroxyalkyl, or aralkyl, more typically $(C_8-C_{22})$alkyl, and p is an integer of from 1 to 10.

Suitable alkylpolyglucosides include, for example, $(C_8-C_{10})$alkylpolyglucoside.

Imidazoline-based amphoteric surfactants are generally known. In one embodiment, the imidazoline-based amphoteric surfactant comprises an agronomically acceptable salt of a substituted imidazoline compound according to structure (III):

$$R^4-\overset{\overset{O}{\|}}{C}-\overset{H}{\underset{}{N}}-CH_2CH_2-\overset{\overset{R^5}{|}}{\underset{R^7}{N}}-R^6 \quad (III)$$

wherein:

$R^4$ is alkyl alkenyl, or aryl, more typically $(C_8-C_{18})$alkyl, $R^5$ is $R^8COOH$ or $R^9SO_3H$, $R^6$ is H, alkyl, hydroxyalkyl, $R^8COOH$, or $R^9SO_3H$, $R^7$ is absent, H, alkyl, hydroxyalkyl, $R^8COOH$, or $R^9SO_3H$, provided that if $R^7$ is H, alkyl, hydroxyalkyl, $R^8COOH$, or $R^9SO_3H$, then the nitrogen atom to which $R^5$, $R^6$, and $R^7$ are each bonded carries a positive charge, and $R^8$ and $R^9$ are each independently alkylene, more typically methylene, dimethylene or trimethylene, which may optionally be substituted on one or more carbon atoms with hydroxyl.

In one embodiment, $R^4$ is $(C_8-C_{18})$alkyl, $R^5$ is $R^8COOH$, $R^6$ is $(C_1-C_6)$alkyl, $R^7$ is H, and $R^8$ is methylene or dimethylene.

In one embodiment, $R^4$ is $(C_8-C_{18})$alkyl, $R^5$ and $R^6$ are each $R^8COOH$, $R^7$ is hydroxy$(C_1-C_6)$alkyl, and $R^8$ is methylene or dimethylene.

In one embodiment, $R^4$ is $(C_8-C_{18})$alkyl, $R^5$ is $R^9SO_3H$, $R^6$ is hydroxy$(C_1-C_6)$alkyl, $R^7$ is absent, and $R^9$ is:

$$-\overset{H_2}{C}-\overset{\overset{OH}{|}}{\underset{H}{C}}-\overset{H_2}{C}-.$$

Suitable Imidazoline-based amphoteric surfactants include the alkali metal, alkaline earth metal, ammonium or substituted ammonium salts of cocoamphoacetate cocoamphopropionate, cocoamphodiacetate, lauroamphoacetate, lauroamphodiacetate, lauroamphodipropionate, lauroamphodiacetate, caproamphodiacetate, caproamphoacetate, caproamphodipropionate, and stearoamphoacetate.

Sultaine surfactants are generally known. In one embodiment, the sultaine surfactant comprises at least one compound according to structure (IV):

$$R^{10}-\overset{\overset{O}{\|}}{C}-\overset{H}{\underset{}{N}}-CH_2CH_2CH_2-\overset{+}{H}N-\overset{\overset{R^{11}}{|}}{\underset{R^{12}}{C}}-\overset{H_2}{\underset{H}{C}}-\overset{\overset{OH}{|}}{\underset{}{C}}-\overset{H_2}{C}-SO_3^- \quad (IV)$$

wherein:

$R^{10}$ is alkyl alkenyl, or aryl, more typically $(C_2-C_{18})$alkyl, and $R^{11}$ and $R^{12}$ are each alkyl.

Suitable sultaine surfactants include, for example, lauryl hydroxy sultaine, laurimidopropyl hydroxysultaine, cocoamidopropylhydroxy sultaine, oleamidopropyl hydroxysultaine, tallowamidopropyl hydroxysultaine, alkylether hydroxypropyl sultaine, and mixtures thereof.

Aminopropionate surfactants are generally known. In one embodiment, the aminopropionate surfactant comprises at least one compound according to structure (V):

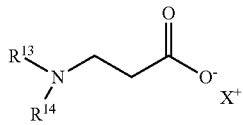
(V)

wherein
$R^{13}$ is alkyl, alkenyl, aryl or aralkyl
$R^{14}$ is H, alkyl, alkenyl, aryl or aralkyl, and
$X^+$ is an agronomically acceptable cation.

In one embodiment, $R^{13}$ is $(C_8-C_{22})$alkyl and $R^{14}$ is H.

Suitable aminopropionate surfactants include, for example, sodium $(C_8-C_{22})$alkylaminopropionate surfactants.

Sulfonate surfactant compounds are generally known compounds and include agronomically acceptable salts of mono-sulfonic acids, agronomically acceptable salts of di-sulfonic acids, and mixtures thereof. In one embodiment, the adjuvant composition comprises one or more sulfonate surfactant compounds according to structure (VI) or (VII):

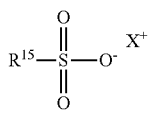
(VI)

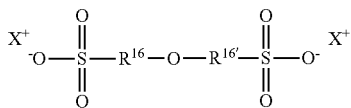
(VII)

wherein:
$R^{15}$ is aryl, aryloxy, or alkenyl,
$R^{16}$ and $R^{16'}$ are each independently arylene, and
$X^+$ is an agronomically acceptable cation.

In one embodiment, $R^{15}$ is phenyl, $(C_8-C_{18})$alkylphenyl, or $(C_8-C_{18})$alkylphenoxy.

In one embodiment, $R^{16}$ and $R^{16'}$ are each $(C_8-C_{18})$alkylphenylene.

Suitable sulfonate surfactant compounds include, for example, sodium cocoamphohydroxypropyl sulfonate, calcium dodecylbenzene sulfonate, calcium octadecylphenyl sulfonate, sodium tridecyl benzene sulfonate, isopropylamine dodecyl benzene sulfonate, isopropylamine tridecyl benzene sulfonate, ammonium tridecyl phenyl sulfonate, sodium $(C_8-C_{18})$alkylphenoxysulfonate, sodium xylene sulfonate, sodium $(C_{14}-C_{16})$alpha olefin sulfonate, disodium alkyldiphenyloxide disulfonates, and mixtures thereof.

Sulfosuccinate surfactant compounds are generally known compounds and include agronomically acceptable salts of mono-esters of sulfosuccinic acid, agronomically acceptable salts of di-esters of sulfosuccinic acid, each of which may, optionally, be alkoxylated, as well as mixtures thereof. In one embodiment, the adjuvant composition comprises one or more sulfosuccinate surfactant compounds according to structure (VIII):

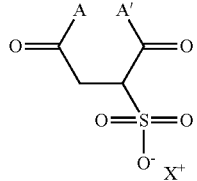
(VIII)

wherein:
A and A' are each independently —O⁻X⁺, or

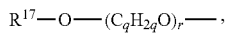

provided that at least one of A and A' is

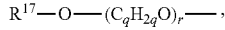

each $R^{17}$ is independently H, alkyl, aryl, or alkylamidoalkyl,
q is 2, 3, or 4, provided, if r is greater than 1, that q may differ independently for each $(C_qH_{2q}O)$ repeat unit,
each r is independently 0 or an integer of from 1 to about 100, more typically from 1 to 50, and
each $X^+$ is an agronomically acceptable cation.

In one embodiment, one of A and A' is —O⁻X⁺, and the other of A and A' is

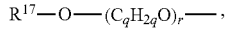

wherein r is 0 or an integer of from 1 to about 20, and $R^{17}$ is $(C_6-C_{18})$alkyl, $(C_1-C_{18})$alkylphenyl, or $(C_6-C_{18})$alkylamido$(C_2-C_6)$alkyl.

In one embodiment, A and A' are each

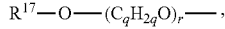

wherein each r is independently 0 or an integer of from 1 to about 20, and each $R^{17}$ is $(C_6-C_{18})$alkyl, $(C_1-C_{18})$alkylphenyl, or $(C_6-C_{18})$alkylamido$(C_2-C_6)$alkyl.

Suitable sulfosuccinate surfactant compounds include, for example, disodium monooctylsulfosuccinate, sodium dioctylsulfosuccinate, disodium lauryl sulfosuccinate, disodium laureth sulfosuccinate, disodium laurimide (MEA) sulfosuccinate, disodium mono-alkylphenyl ether sulfosuccinate, and mixtures thereof.

Alkyl ether carboxylate surfactant compounds are generally known and include agronomically acceptable salts of alkoxylated carboxylic acids. In one embodiment, the adjuvant composition comprises one or more alkyl ether carboxylate surfactant compounds according to structure (IX):

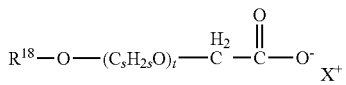

wherein:
R$^{18}$ is alkyl, alkenyl, aryl, aryloxy, or aralkyl,
s is 2, 3, or 4, provided, if t is greater than 1, that s may differ independently for each (C$_s$H$_{2s}$O) repeat unit,
t is 0 or an integer of from 1 to 100, more typically an integer of from 1 to 50, and
X$^+$ is an agronomically acceptable cation.

In one embodiment, s is 2 or 3 and r is an integer of from 1 to about 10.

In one embodiment, R$^{18}$ is (C$_8$-C$_{18}$)alkyl.

Suitable alkyl ether carboxylate surfactant compounds include, for example, sodium laureth-13 carboxylate, alkyl polyether carboxylic acids.

Alkoxylated fatty acid surfactant compounds are generally known compounds. The fatty acid portion of such alkoxylated fatty acid surfactant compounds is typically derived from a saturated or unsaturated mono- or di- fatty acids, typically (C$_6$-C$_{30}$)fatty acids, such as, for example, lauric acid, myristic acid, palmitic acid, stearic acid, oleic acid, linoleic acid, behenic acid, erucic acid, or a mixture thereof, including vegetable oils, such as, for example, tall oil, rapeseed oil, canola oil, soy oil, coconut oil, castor oil, corn oil, olive oil, sunflower oil, cottonseed oil, palm oil, peanut oil, sesame oil, safflower oil, linseed oil, flax seed oil, palm kernel oil, and mixtures thereof. These acids are alkoxylated with from 2 to 20 moles, more typically from 5 to 20 moles. of a (C$_2$-C$_4$) alkylene oxide, more typically, ethylene oxide.

Alkoxylated alcohol surfactant compounds are generally known. In one embodiment, the adjuvant composition comprises one or more alkoxylated alcohol surfactant compounds according to structure (X):

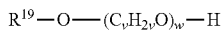

wherein
R$^{19}$ is alkyl or alkenyl,
v is 2, 3, or 4, provided, if w is greater than 1, that v may differ independently for each (C$_v$H$_{2v}$O) repeat unit, and
w is an integer of from 1 to 100, more typically from 1 to 50, or an agronomically acceptable salt thereof.

In one embodiment, q is an integer of from 1 to about 30.
In one embodiment, R$^{19}$ is (C$_6$-C$_{22}$)alkyl.

Suitable alkoxylated alcohol surfactant compounds include, for example, ethoxylated (15) tridecyl alcohol, ethoxylated (7) lauryl alcohol, ethoxylated (20) oleyl alcohol, ethoxylated (15) stearyl alcohol, and mixtures thereof.

In one embodiment, the adjuvant composition comprises, based on 100 parts by weight ("pbw") of the adjuvant composition, from about 0.1 to about 25 pbw, more typically from about 0.5 to about 15 pbw of at least one surfactant compound selected from each of at least two of the following groups:
(i) phosphate ester surfactants,
(ii) alkylpolyglucoside surfactants,
(iii) the group consisting of imidazoline-based amphoteric surfactants, sultaine surfactants, and aminopropionate surfactants, and
(iv) the group consisting of sulfonate surfactants, sulfosuccinate surfactants, alkyl ether carboxylate surfactants, alkoxylated fatty acid surfactants, and alkoxylated alcohol surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from phosphate ester surfactants, and from about 0.1 to about 25 pbw, more typically from about 0.5 to about 15 pbw, of at least one surfactant compound selected from alkylpolyglucoside surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from phosphate ester surfactants and from about 0.1 to about 25 pbw, more typically from about 0.5 to about 15 pbw, of at least one surfactant compound selected from the group consisting of imidazoline-based amphoteric surfactants, sultaine surfactants, and aminopropionate surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from phosphate ester surfactants and from about 0.1 to about 25 pbw, more typically from about 0.5 to about 15 pbw, of at least one surfactant compound selected from the group consisting of sulfonate surfactants, sulfosuccinate surfactants, alkyl ether carboxylate surfactants, alkoxylated fatty acid surfactants, and alkoxylated alcohol surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from alkylpolyglucoside surfactants and from about 0.1 to about 25 pbw, more typically from about 0.5 to about 15 pbw, of at least one surfactant compound selected from the group consisting of imidazoline-based amphoteric surfactants, sultaine surfactants, and aminopropionate surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from alkylpolyglucoside surfactants and from about 0.1 to about 25 pbw, more typically from about 0.5 to about 15 pbw, of at least one surfactant compound selected from the group consisting of sulfonate surfactants, sulfosuccinate surfactants, alkyl ether carboxylate surfactants, alkoxylated fatty acid surfactants, and alkoxylated alcohol surfactants.

In one embodiment, the adjuvant composition comprises, based on 100 pbw of the adjuvant composition, from about 0.1 to about 25 pbw, more typically from about 0.5 to about 15 pbw, of at least one surfactant compound selected from the group consisting of imidazoline-based amphoteric surfactants, sultaine surfactants, and aminopropionate surfactants, and from about 0.1 to about 25 pbw, more typically from about 0.5 to about 15 pbw, of at least one surfactant compound selected from the group consisting of sulfonate surfactants, sulfosuccinate surfactants, alkyl ether carboxylate surfactants, alkoxylated fatty acid surfactants, and alkoxylated alcohol surfactants.

Suitable pesticides are biologically active compounds used to control agricultural pests and include, for example, herbicides, plant growth regulators, crop dessicants, fungicides, bacteriocides, bacteriostats, insecticides, and insect repellants. Suitable pesticides include, for example, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glyphosate salts and esters; dihalobenzonitrile herbicides such as bromoxynil, or ioxynil, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoximmethyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources such as, for example, the *Compendium of Pesticide Common Names*, which is available on-line at http://www.hclrss.demon.co.uk/index.html.

In one embodiment, the pesticide comprises one or more compounds selected from , herbicides, plant growth regulators, crop dessicants, fungicides, bacteriocides, bacteriostats, insecticides, miticides, nematocides, insect repellants and mixtures thereof.

In one embodiment, the pesticide is selected from glufosinate, glyphosate, water soluble glufosinate salts, water soluble glyphosate salts, and mixtures thereof, including, for example sodium, potassium, isopropyl amine, or ammonium salts.

In one embodiment, the pesticide is selected from, the potassium salt of glyphosate, the sodium salt of glyphosate, the isopropyl amine salt of glyphosate, the ammonium salt of glyphosate, and mixtures thereof.

Herbicidal compositions containing glyphosate or derivatives thereof are used to control a very wide variety of plants worldwide and can, when applied to the target plant in a herbicidally effective amount, reportedly control one or more target plant species of one or more of the following genera: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Portulaca, Pteridium, Pueraria, Rubus, Salsola, Setaria, Sida, Sinapis, Sorghum, Triticum, Typha, Ulex, Xanthium* and *Zea*, including annual broadleaf species such as, for example, velvetleaf (*Abutilon theophrasti*), pigweed (*Amaranthus* spp.), lamb's quarter (*Chenopodiaeae* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia* scoparia), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis arvensis*) and cocklebur (*Xanthium* spp.), annual narrowleaf species such as for example, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), hemp sesbania (*Sesbania exaltata*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*), perennial broadleaf species such as, for example, mugwort (*Artemisia* spp.), milkweed (*Asclepias* spp.), canada thistle (*Cirsium arvense*), field bindweed (*Convolvulus arvensis*) and kudzu (*Pueraria* spp.), perennial narrowleaf species such as for example, brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.), and other perennial species such as, for example, horsetail (*Equisetum* spp.), bracken (*Pteridium aquilinum*), blackberry (*Rubus* spp.) and gorse (*Ulex europaeus*), and sickle pod.

As used herein, the terminology "effective amount" in reference to the relative amount of a pesticide in a pesticide composition means the relative amount of pesticide that is effective to control a target pest, for example, a target plant, fungus, bacterium, or insect, when the pesticide composition is applied at a given application rate.

In one embodiment, the pesticide is glyphosate herbicide and the pesticide composition is an herbicide composition that comprises a herbicidally effective amount of glyphosate.

As used herein, the terminology "an herbicidally effective amount" in reference to the relative amount of herbicide in an herbicidal composition means the relative amount that is effective to control growth of a target plant when the herbicidal composition is spray applied to the target plant at a given application rate.

In one embodiment, the pesticide composition comprises, based on 100 parts by weight ("pbw") of the pesticide composition,
(a) from about 0.001 to about 2 pbw of at least one surfactant compound selected from each of at least two of the following groups:
  (i) phosphate ester surfactants,
  (ii) alkylpolyglucoside surfactants,
  (iii) the group consisting of imidazoline-based amphoteric surfactants, sultaine surfactants, and aminopropionate surfactants, and (iv) the group consisting of sulfonate surfactants, sulfosuccinate surfactants, alkyl ether carboxylate surfactants, alkoxylated fatty acid surfactants, and alkoxylated alcohol surfactants, and (b) an effective amount of a pesticide In one embodiment, the pesticide composition comprises, based on 100 pbw of the pesticide composition, (a) from about 0.001 to about 2 pbw of at least one surfactant compound selected from phosphate ester surfactants, and from about 0.001 to about 2 pbw of at least one surfactant compound selected from alkylpolyglucoside surfactants, and (b) an effective amount of a pesticide.

In one embodiment, the pesticide composition comprises, based on 100 pbw of the pesticide composition, (a) from about 0.001 to about 2 pbw of at least one surfactant compound selected from phosphate ester surfactants and from about 0.001 to about 2 pbw of at least one surfactant compound selected from the group consisting of imidazoline-based amphoteric surfactants, sultaine surfactants, and aminopropionate surfactants, and (b) an effective amount of a pesticide.

In one embodiment, the pesticide composition comprises, based on 100 pbw of the pesticide composition, (a) from about 0.001 to about 2 pbw of at least one surfactant compound selected from phosphate ester surfactants and from about 0.001 to about 2 pbw of at least one surfactant compound selected from the group consisting of the group consisting of sulfonate surfactants, sulfosuccinate surfactants, alkyl ether carboxylate surfactants, alkoxylated fatty acid surfactants, and alkoxylated alcohol surfactants, and (b) an effective amount of a pesticide.

In one embodiment, the pesticide composition comprises, based on 100 pbw of the pesticide composition, (a) from about 0.001 to about 2 pbw of at least one surfactant compound selected from alkylpolyglucoside surfactants from about 0.001 to about 2 pbw of at least one surfactant compound selected from the group consisting of imidazoline-based amphoteric surfactants, sultaine surfactants, and aminopropionate surfactants, and (B) an effective amount of a pesticide.

In one embodiment, the pesticide composition comprises, based on 100 pbw of the pesticide composition, (a) from about 0.001 to about 2 pbw of at least one surfactant compound selected from alkylpolyglucoside surfactants from about 0.001 to about 2 pbw of at least one surfactant compound selected from the group consisting of the group consisting of sulfonate surfactants, sulfosuccinate surfactants, alkyl ether carboxylate surfactants, alkoxylated fatty acid surfactants, and alkoxylated alcohol surfactants, and (b) an effective amount of a pesticide.

In one embodiment, the pesticide composition comprises, based on 100 pbw of the pesticide composition, (a) from about 0.001 to about 2 pbw of at least one surfactant compound selected from the group consisting of imidazoline-based amphoteric surfactants, sultaine surfactants, and aminopropionate surfactants, and from about 0.001 to about 2 pbw of at least one surfactant compound selected from the group consisting of the group consisting of sulfonate surfactants, sulfosuccinate surfactants, alkyl ether carboxylate surfactants, alkoxylated fatty acid surfactants, and alkoxylated alcohol surfactants, and (b) an effective amount of a pesticide.

In one embodiment, the pesticide component of the pesticide composition comprises an effective amount of glyphosate, more typically an amount, based on 100 pbw of the pesticide composition, of from about 10 pbw to about 90 pbw, even more typically from about 30 to about 60 pbw, glyphosate.

The adjuvant and pesticide compositions of the present invention may each, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons.

In one embodiment, the adjuvant composition of the present invention further comprises, based on 100 pbw of such composition, up to about 25 pbw an organic solvent.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example 0-0-1 3%-S, 3%-Zn, 2%-Fe, 2%-Mn, and mixtures thereof. In one embodiment, the pesticide composition comprises from about 85 to about 99 pbw, more typically from about 90 to about 99 pbw, and even more typically from about 93 to about 99 pbw, of a mixture of fertilizer and water.

In one embodiment, the pesticide composition of the present invention further comprises one or more water conditioners, such as for example, chelating agents, such as ethylenediamine tetraacetic acid, complexing agents such as ammonium sulfate, and pH adjusting agents, such as citric acid and polyacrylic acid.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

The pesticide composition of the present invention may, optionally, further comprise other ingredients, such as one or more additional surfactants, one or more thickeners, such as polysaccharide thickeners, and polyacrylamide thickeners, as well as antifoams, spreaders, and drift control agents.

The adjuvant composition of the present invention is made by combining and mixing the components of such composition.

The pesticide composition of the present invention is made by mixing the ingredients together. In one embodiment, the pesticide composition is made by combining and mixing the adjuvant composition of the present invention, a pesticide compound, and water. Alternatively, the pesticide composition is made by combining and mixing the separate components of the adjuvant composition, a pesticide, and water.

The pesticide composition of the present invention is useful for treating plant to control pests, such as for example, depending on the choice of pesticide, killing, discouraging the growth of, or repelling plants, bacteria, fungi, insects, or other pests.

In one embodiment, the pesticide composition is spray applied to foliage of a target plant at a rate of from about 0.5 pint/acre to about 3 pints/acre, more typically from about 0.5 pint/acre to about 2.5 pints/acre.

The invention claimed is:
1. A pesticide composition, comprising
 (a) at least one surfactant compound selected from each of the following groups:
  (i) alkylpolyglucoside surfactants, wherein the alkyl polyglucoside comprises C8-C10 alkylpolyglucoside,

(ii) the group consisting of imidazoline-based amphoteric surfactants, wherein the imidazoline-based amphoteric surfactant is selected from at least one member of the group consisting of the alkali metal, alkaline earth metal, ammonium or substituted ammonium salts of cocoamphopropionate, wherein the parts by weight of alkylpolyglucoside surfactant to imidazoline-based amphoteric surfactant is 0.5 to 15:0.5 to 15, (b) 10 to 90 pbw of a pesticide per 100 pbw of said pesticide composition, wherein the pesticide is selected from at least one member of the group consisting of dimethylamine glyphosate and isopropylamine glyphosate; and (c) water.

2. The pesticide composition of claim 1, further comprising at least one member of the group consisting of:
one or more agronomically acceptable organic solvents selected from alkylated aromatic solvents and mineral oil fractions;
a fertilizer for providing the primary nutrients of nitrogen, phosphorus and/or potassium selected from urea ammonium nitrate secondary nutrients sulfur, calcium, magnesium, ammonium thiosulfate, micronutrient fertilizers containing zinc, iron, molybdenum, copper, boron, chlorine, magnesium, and mixtures thereof;
one or more water conditioners selected from ethylenediamine tetraacetic acid, ammonium sulfate, citric acid, and polyacrylic acid;
one or more thickeners selected from polysaccharide thickeners, and polyacrylamide thickeners, antifoams, spreaders, and drift control agents; and
second pesticide selected from at least one member of the group consisting of herbicides, fungicides, insecticides, miticides, and carbamate nematicides:
wherein the herbicide is selected from the group consisting of:
triazine herbicides selected from metribuzin, hexaxinone, or atrazine;
sulfonylurea herbicides, chlorsulfuron; uracils, lenacil, bromacil, or terbacil;
urea herbicides, linuron, diuron, siduron, or neburon; acetanilide herbicides, alachlor, or metolachlor, thiocarbamate, benthiocarb, triallate;
oxadiazolone herbicides selected from oxadiazon;
phenoxyacetic acids selected from 2,4-D;
diphenyl ether herbicides selected from fluazifop, acifluorfen, bifenox, or oxyfluorfen;
dinitro aniline herbicides selected from trifluralin;
dihalobenzonitrile herbicides selected from bromoxynil, ioxynil, dipyridilium herbicides, and paraquat;
wherein the fungicides are selected from the group consisting of:
nitrilo oxime fungicides selected from cymoxanil;
imidazole fungicides selected from benomyl, carbendazim, or thiophanate-methyl;
triazole fungicides selected from triadimefon;
sulfenamide fungicides selected from captan;
dithio-carbamate fungicides selected from maneb, mancozeb, or thiram;
chlorinated aromatic fungicides selected from chloroneb;
dichloro aniline fungicides selected from iprodione, strobilurin fungicides selected from kresoxim-methyl, trifloxystrobin or azoxystrobin;
chlorothalonil;
copper salt fungicides selected from copper oxychloride;
sulfur; phenylamides; and
acylamino fungicides selected from metalaxyl or mefenoxam;
wherein the insecticides are selected from the group consisting of:
carbamate insecticides selected from methomyl, carbaryl, carbofuran, or aldicarb;
organo thiophosphate insecticides selected from EPN, isofenphos, isoxathion, chlorpyrifos, or chlormephos;
organophosphate insecticides selected from terbufos, monocrotophos, or terachlorvinphos;
perchlorinated organic insecticides selected from methoxychlor;
synthetic pyrethroid insecticides selected from fenvalerate, abamectin or emamectin benzoate, neonicotinoide insecticides selected from thiamethoxam or imidacloprid;
pyrethroid insecticides selected from lambda-cyhalothrin, cypermethrin or bifenthrin, and
oxadiazine insecticides selected from indoxacarb, imidachlopryd, or fipronil;
wherein the miticides are selected from the group consisting of:
propynyl sulfite miticides selected from propargite;
triazapentadiene miticides selected from amitraz;
chlorinated aromatic miticides selected from chlorobenzilate, or tetradifan;
and dinitrophenol miticides selected from binapacryl; and
wherein the carbamate nematicides are selected from oxamyl.

3. The composition of claim 2, wherein the second pesticide is selected from the group consisting of fungicides, insecticides, miticides, and carbamate nematicides:
wherein the fungicides are selected from the group consisting of:
nitrilo oxime fungicides selected from cymoxanil;
imidazole fungicides selected from benomyl, carbendazim, or thiophanate-methyl;
triazole fungicides selected from triadimefon;
sulfenamide fungicides selected from captan;
dithio-carbamate fungicides selected from maneb, mancozeb, or thiram;
chlorinated aromatic fungicides selected from chloroneb;
dichloro aniline fungicides selected from iprodione,
strobilurin fungicides selected from kresoxim-methyl, trifloxystrobin or azoxystrobin;
chlorothalonil;
copper salt fungicides selected from copper oxychloride;
sulfur; phenylamides; and
acylamino fungicides selected from metalaxyl or mefenoxam;
wherein the insecticides are selected from the group consisting of:
carbamate insecticides selected from methomyl, carbaryl, carbofuran, or aldicarb;
organo thiophosphate insecticides selected from EPN, isofenphos, isoxathion, chlorpyrifos, or chlormephos;
organophosphate insecticides selected from terbufos, monocrotophos, or terachlorvinphos;
perchlorinated organic insecticides selected from methoxychlor;

synthetic pyrethroid insecticides selected from fenvalerate, abamectin or emamectin benzoate, neonicotinoide insecticides selected from thiamethoxam or imidacloprid;

pyrethroid insecticides selected from lambda-cyhalothrin, cypermethrin or bifenthrin, and oxadiazine insecticides selected from indoxacarb, imidachlopryd, or fipronil;

wherein the miticides are selected from the group consisting of:

propynyl sulfite miticides selected from propargite;

triazapentadiene miticides selected from amitraz;

chlorinated aromatic miticides selected from chlorobenzilate, or tetradifan;

and dinitrophenol miticides selected from binapacryl; and wherein the carbamate nematicides are selected from oxamyl.

4. The composition of claim 1, wherein the imidazoline amphoteric based surfactant comprises at least one member of the group consisting of alkali salt of cocoamphodipropionate.

5. The composition of claim 1, wherein the imidazoline amphoteric based surfactant comprises sodium salt of cocoamphodipropionate.

6. The pesticide composition of claim 1, further comprising said at least one member of the group consisting of:

one or more agronomically acceptable organic solvents selected from alkylated aromatic solvents and mineral oil fractions;

a fertilizer for providing the primary nutrients of nitrogen, phosphorus and/or potassium selected from urea ammonium nitrate secondary nutrients sulfur, calcium, magnesium, ammonium thiosulfate micronutrient fertilizers containing zinc, iron, molybdenum, copper, boron, chlorine, magnesium, and mixtures thereof;

one or more water conditioners selected from ethylenediamine tetraacetic acid, ammonium sulfate, citric acid, and polyacrylic acid; and one or more thickeners selected from polysaccharide thickeners, and polyacrylamide thickeners, antifoams, spreaders, and drift control agents.

7. A method for treating a target plant, comprising applying to such plant a pesticide composition of claim 1.

8. The method of claim 7, wherein component (a) of the pesticide composition comprises based on 100 parts by weight of the pesticide composition, from about 0.001 to about 2 parts by weight of at least one surfactant compound selected from alkylpolyglucoside surfactants from about 0.001 to about 2 parts by weight of at least one surfactant compound selected from the group consisting of imidazoline-based amphoteric surfactants.

9. The method of claim 7, wherein the pesticide composition is spray applied to foliage of the target plant at a rate of from about 0.5 pint of the pesticide composition per acre to about 3 pints of the pesticide composition per acre.

\* \* \* \* \*